US00PP34119P2

(12) United States Plant Patent
Gräb

(10) Patent No.: US PP34,119 P2
(45) Date of Patent: Apr. 12, 2022

(54) CHERRY TREE NAMED 'KSG 03 A'

(50) Latin Name: *Prunus avium*
Varietal Denomination: KSG 03 A

(71) Applicant: Lizenzen für Früchte und Pflanzen GmbH, Bassenheim (DE)

(72) Inventor: Hilmar Gräb, Bassenheim (DE)

(73) Assignee: Lizenzen für Früchte und Pflanzen GmbH, Bassenheim (DE)

( * ) Notice: Subject to any disclaimer, the term of this patent is extended or adjusted under 35 U.S.C. 154(b) by 0 days.

(21) Appl. No.: 17/300,401

(22) Filed: Jun. 14, 2021

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ... A01H 5/08; A01H 5/02; A01H 5/00; A01H 6/74; A01H 6/7427; A01H 6/7445
See application file for complete search history.

(56) References Cited

PUBLICATIONS

Blatt Fur Sortenwesen, retrieved on Aug. 23, 2021, retrieved from the Internet at https://docplayer.org/178817780-51-jahrgang-heft-11-hannover-den-15-november-2018-seite-inhalt-bekanntmachungen-nach-dem-stand-vom-1-november-2018.html, 51 Jahrgang, Heft 11, 2018, 223 and 227. (Year: 2018).*

Google English translation retrieved on Aug. 31, 2021, retrieved from the Internet at https://translate.google.com/?sl=auto&tl=en&text=Blatt%20Fur%20Sortenwesen%20Amtsblatt%20des%20Bundessortenamtes%20%0AObstarten%20auber%20Ziersorten%0ASubkirsche%20&op=translate, one page. (Year: 2021).*

CPVO Register 4.1.23 for Prunus 'KSG 03 A', retrieved on Jan. 5, 2022, retrieved from the Internet at https://online.plantvarieties.eu/publicConsultationDetails?registerId=20191935&denomination=ksg%2003%20a, 3 pp. (Year: 2022).*

UPOV Pluto 20220104 DE KIA 00114 PBR for KSG 03 A, retrieved on Jan. 5, 2022, retrieved from the Internet at https://pluto.upov.int/result, one page. (Year: 2022).*

* cited by examiner

*Primary Examiner* — June Hwu
(74) *Attorney, Agent, or Firm* — Michelle Bos Legal LLC

(57) ABSTRACT

'KSG 03 A' is a self-fruitful sweet cherry tree distinguished by its very late maturity and moderate to high yield of fruit with excellent firmness and flavor.

5 Drawing Sheets

Latin name: *Prunus avium.*
Variety denomination: 'KSG 03 A'.

BACKGROUND AND SUMMARY OF THE VARIETY

The new sweet cherry tree 'KSG 03 A' originated in the applicant's breeding program, where it was selected from seedlings obtained from the open pollination of female parent 'Sumtare' (not patented) by an unknown male parent at Kettig, Germany in 2004. Initial asexual propagation by grafting and budding was carried out at Kettig in 2006. 'KSG 03 A' was initially selected for its very late harvest maturity, which occurs two weeks after 'Sumtare'. Upon further observation, fruit of 'KSG 03 A' was further distinguished by its moderate to high yield of fruit with excellent firmness and flavor.

'KSG 03 A' is similar to sweet cherry variety '13S2009' (U.S. Plant Pat. No. 20,551) in that both varieties are self-fertile, bloom around the same time, and produce similarly-colored fruit. Fruit of 'KSG 03 A' matures later, and is firmer and less prone to cracking than '13S2009'.

'KSG 03 A' is distinguished from related variety 'KSG 24 A' (Ser. No. 147/300,411) by its firmer, slightly smaller fruit, later harvest maturity, and more vigorous growth habit.

The 'KSG 03 A' cherry tree has been found to exhibit its distinctive characteristics and remain stable through successive asexually propagated generations.

BRIEF DESCRIPTION OF THE PHOTOGRAPHS

The accompanying photographs, taken in 2016 at Kettig, Germany, show 10-year-old trees grown on Gisela® 5 rootstock ('GI 148/2', U.S. Plant Pat. No. 9,622).

Figure 1:
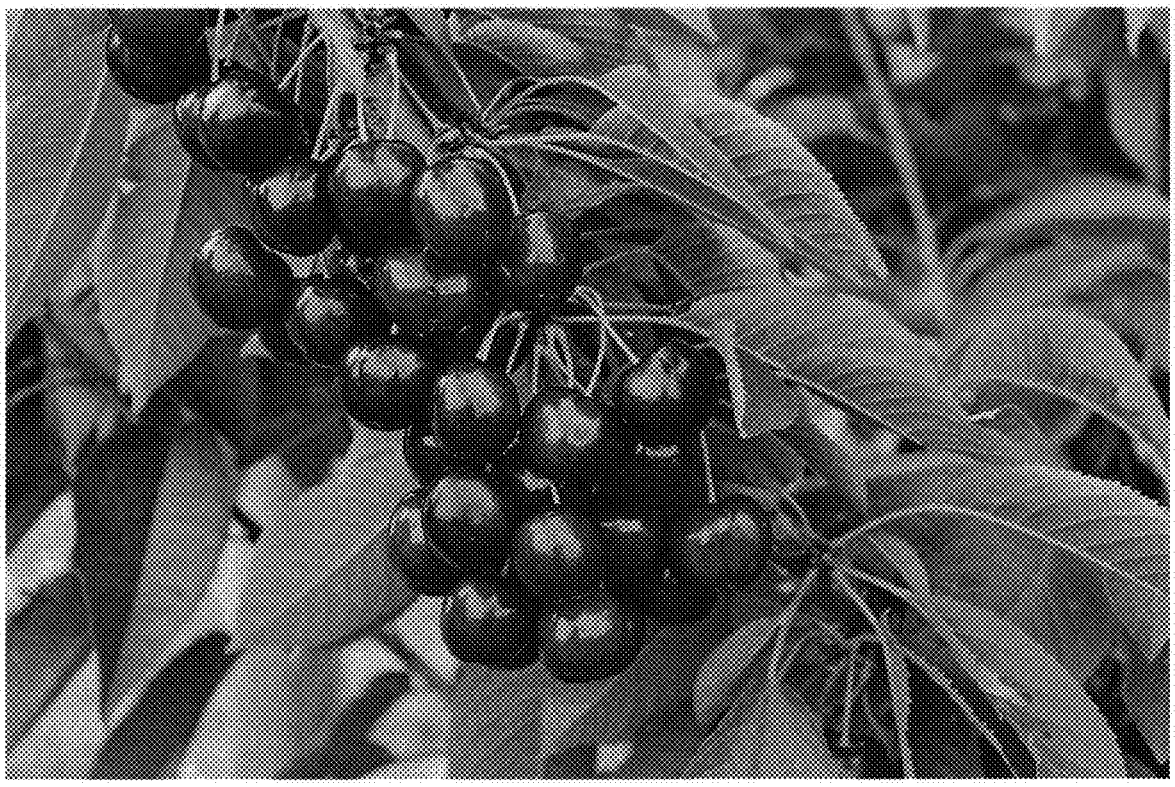
FIG. 1 shows the fruit and leaves of 'KSG 03 A'.
Figure 2:
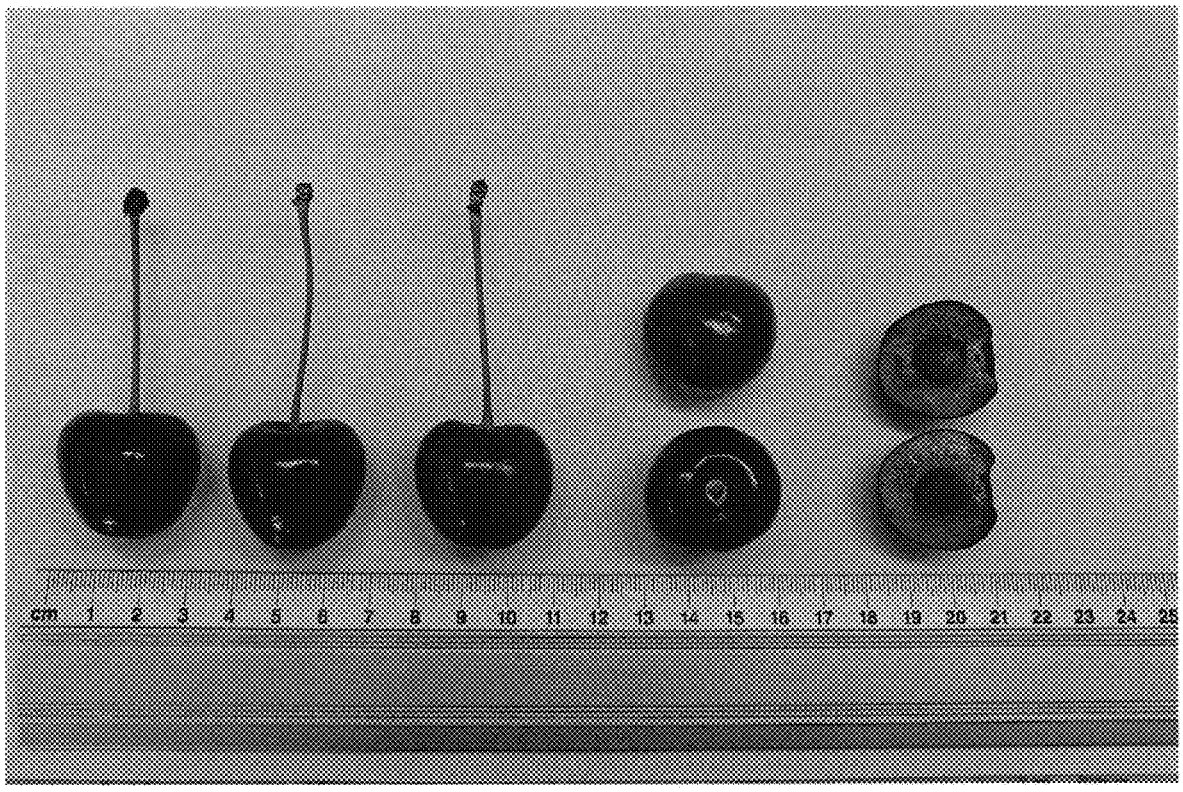
FIG. 2 shows the fruit of 'KSG 03 A'.
Figure 3:
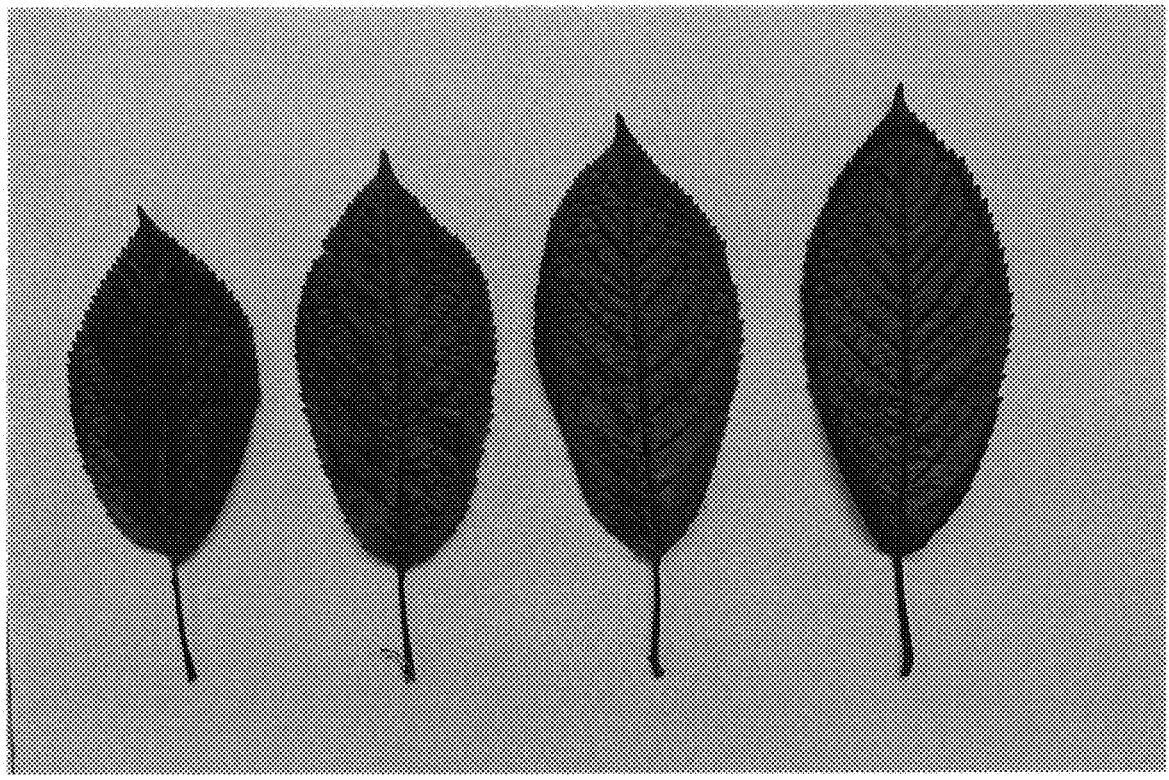
FIG. 3 shows the leaves of 'KSG 03 A'.
Figure 4:
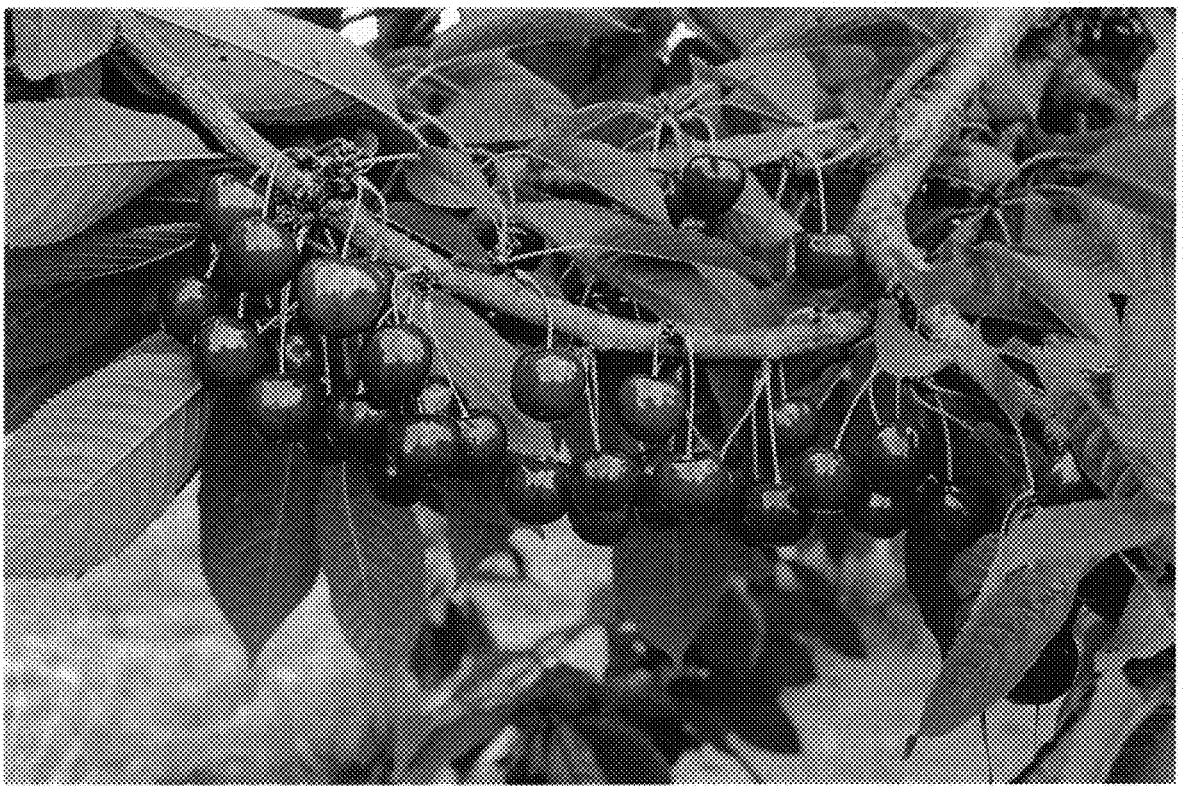
FIG. 4 shows a branch, fruit and leaves of 'KSG 03 A'.
Figure 5:
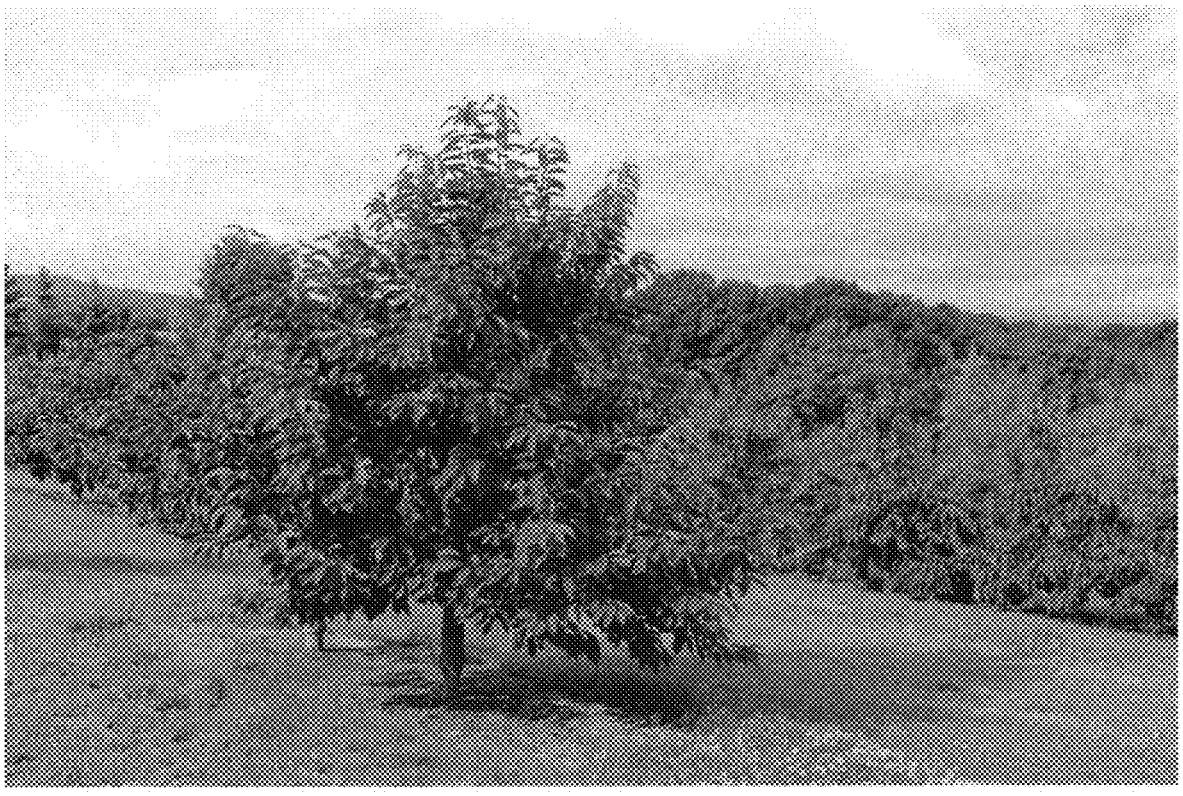
FIG. 5 shows a tree of 'KSG 03 A'.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations recorded in 2016 at Kettig, Germany, of 10-year-old trees grown on Gisela® 5 rootstock. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart (Royal Horticultural Society, 6th ed.).

Tree:

*Vigor*.—Medium-strong.
*Habit, shape*.—Spreading.
*Density*.—Dense.
*Branching*.—Medium to strong.
*Height*.—3.2 m.
*Spread*.—3.8 m.
*Trunk diameter*.—11 cm at 80 cm above the graft.
*Trunk texture*.—Slightly rough.
*Bark color*.—Greyed-purple N186C.
*Lenticel length*.—5 mm to 9 mm.
*Lenticel width*.—1.5 mm to 2.0 mm.
*Lenticel color*.—Greyed-orange 167B.
*Lenticel density*.—Dense.
*Production*.—Precocious, moderate to high yield; 16 kg per tree (Gisela® 5 rootstock, central leader system).

One-year-old shoots:

*Diameter*.—6.5 mm.
*Surface texture*.—Slightly fluted.
*Color*.—Grey-brown N199C.
*Crotch angle*.—Upright to spreading.
*Buds*.—Alternate arrangement, average internode length, slightly raised, acute tip.
*Lenticel length*.—1 mm to 3 mm.
*Lenticel width*.—1 mm to 2 mm.
*Lenticel shape*.—Mostly round.
*Lenticel density*.—Medium.
*Lenticel color*.—Greyed-orange 165B.

Flower buds:

*Pedicel length*.—17 mm.
*Pedicel diameter*.—1.4 mm.
*Pedicel color*.—Yellow-green 144A.
*Bud length*.—11 mm.
*Bud diameter*.—5.5 mm.
*Bud color*.—Green 143A.

Flowers:

*Bloom timing*.—Early to mid-season.
*Bloom duration*.—Moderate, about 8 days.
*Pollination requirement*.—Self-fertile.
*Number of flowers per raceme*.—25 to 30, mostly 4 per unit, high density.
*Flower diameter*.—36 mm to 38 mm.
*Petals*.—5 per flower, overlapping.
*Petal length*.—16 mm.
*Petal width*.—14 mm.
*Petal shape*.—Round to slightly oval with emarginate tip.
*Appearance*.—White, clear shell-shaped venation at base, moderately transparent.
*Margin*.—Smooth.
*Texture*.—Slightly veined.
*Petal color when opening*.—Both surfaces white NN155D with red 39D at tip.
*Petal color when fully open*.—Both surfaces white NN155D.

Sepals:

*Quantity*.—5 per flower.
*Shape*.—Elongated oval.
*Margin*.—Entire, with emargination on each side of base.
*Texture*.—Both surfaces smooth.
*Length*.—8 mm.
*Width*.—3 mm.
*Color*.—Both surfaces green 143B.

Stamens:

*Quantity per flower*.—30 to 35.
*Filament length*.—12 mm.

Anthers:

*Shape*.—Rounded, divided in two.
*Diameter*.—0.7 mm.
*Color*.—Greyed-orange N163A, N163B.

Pistils:

*Quantity*.—1 per flower.
*Length*.—15 mm including stigma and ovary.

Style:

*Length*.—11 mm.
*Color*.—Green 142D.

Stigma:

*Shape*.—Clearly divided in two, T-shaped.
*Color*.—Yellow 2B.

Leaves:

*Length*.—11 cm to 16.5 cm, average 14.2 cm.
*Width*.—6 cm to 8 cm, average 6.9 cm.
*Form*.—Elliptic with acuminate tip and obtuse base.
*Texture*.—Upper surface smooth, moderately glossy.
*Thickness*.—Medium.
*Margin*.—Dentate to serrate.
*Pubescence of upper surface*.—None.
*Pubescence of lower surface*.—Minimal.
*Color of young leaf upper surface*.—Green 143B.
*Color or young leaf lower surface*.—Green 143C.
*Color of mature leaf upper surface*.—Green 137A.
*Color of mature leaf lower surface*.—Green 137C.
*Petiole shape*.—Rounded.
*Petiole length*.—3.9 cm.
*Petiole diameter*.—2.5 mm.
*Petiole color*.—Yellow-green 145A with anthocyanin coloration.
*Venation texture*.—Smooth on leaf upper surface; prominent on lower surface.
*Vein color*.—Green 139C on upper surface; Yellow-green 145A on lower surface.
*Nectaries*.—2 present on petiole near leaf, usually opposite arrangement.
*Nectary shape*.—Round to elongated.
*Nectary color*.—Greyed-purple 183A.

Fruit:

*Maturity when described*.—First picking unless otherwise noted.
*Harvest timing*.—Very late, 3 weeks after 'Regina'.
*Diameter*.—27 mm to 30 mm, average 29 mm.
*Length*.—22 mm to 25 mm, average 24 mm.
*Shape of fruit*.—Slightly oblong heart-shaped.
*Shape of fruit pistil end*.—Flat.
*Skin thickness*.—Medium.
*Tendency to crack*.—Low.
*Skin color at first picking*.—Greyed-purple 187B.
*Skin color at high maturity*.—Greyed-purple 187A.
*Skin lenticels*.—Few on ripe fruit.
*Conspicuousness of suture*.—Weakly conspicuous.
*Flavor*.—First pick, tangy-aromatic with fine acidity; at full maturity, spicy, harmonious, powerful long lasting aroma.
*Soluble solids*.—18° Brix at full maturity.
*Flesh color*.—Red 53B.

*Juice color*.—Red-purple 59B.
*Texture*.—Firm, crunchy, juicy.

Seed:
*Height*.—10.8 mm to 11.7 mm, average 11.3 mm.
*Width*.—9.3 mm.
*Circumference*.—29.18 mm.
*Form*.—Wide elliptic.
*Color*.—Orange-white 159C.

Fruit stem:
*Length*.—41 mm to 51 mm, average 44.6 mm.
*Diameter*.—1.2 mm to 1.7 mm, average 1.4 mm.
*Color*.—Yellow-green 145C.

Market use: Fresh consumption.
Eating quality: Very good.
Storability: Good.
Shipping quality: Good.
Winter hardiness: Tree and buds cold-hardy in area tested.
Disease and pest resistance/susceptibility: Not observed to date.

The invention claimed is:

1. A new and distinct cherry tree named 'KSG 03 A', substantially as illustrated and described.

* * * * *